(12) United States Patent
Larson et al.

(10) Patent No.: US 7,262,859 B2
(45) Date of Patent: Aug. 28, 2007

(54) SYSTEMS AND METHODS FOR MEASUREMENT OPTIMIZATION

(75) Inventors: Jonathan W. Larson, New Ipswich, NH (US); Gregory R. Yantz, Cambridge, MA (US); George Seward, Arlington, MA (US); David Johnson, Edmonton (CA); Jeffrey R. Krogmeier, Woburn, MA (US)

(73) Assignee: U.S. Genomics, Inc., Woburn, MA (US)

( * ) Notice: Subject to any disclaimer, the term of this patent is extended or adjusted under 35 U.S.C. 154(b) by 75 days.

(21) Appl. No.: 11/250,179

(22) Filed: Oct. 13, 2005

(65) Prior Publication Data

US 2006/0160209 A1    Jul. 20, 2006

Related U.S. Application Data

(60) Provisional application No. 60/618,453, filed on Oct. 13, 2004.

(51) Int. Cl.
*G01N 21/55* (2006.01)
*G01N 21/01* (2006.01)

(52) U.S. Cl. .................................... 356/445; 356/244
(58) Field of Classification Search .................. None
See application file for complete search history.

(56) References Cited

U.S. PATENT DOCUMENTS

| | | | |
|---|---|---|---|
| 5,356,776 A | 10/1994 | Kambara et al. | |
| 5,675,155 A | 10/1997 | Pentoncy, Jr. et al. | |
| 5,707,797 A | 1/1998 | Windle | |
| 5,869,001 A | * 2/1999 | Backhaus et al. | 422/58 |
| 6,014,270 A | 1/2000 | Bergmann et al. | |
| 6,100,541 A | 8/2000 | Nagle et al. | |
| 6,210,896 B1 | 4/2001 | Chan | |
| 6,263,286 B1 | 7/2001 | Gilmanshin et al. | |
| 6,355,420 B1 | 3/2002 | Chan | |
| 6,403,311 B1 | 6/2002 | Chan | |
| 6,696,022 B1 | 2/2004 | Chan et al. | |
| 6,762,059 B2 | 7/2004 | Chan et al. | |
| 6,772,070 B2 | 8/2004 | Gilmanshin et al. | |
| 6,790,671 B1 | 9/2004 | Austin et al. | |
| 6,927,065 B2 | 8/2005 | Chan et al. | |
| 2002/0110818 A1 | 8/2002 | Chan | |
| 2002/0119455 A1 | 8/2002 | Chan | |

(Continued)

FOREIGN PATENT DOCUMENTS

WO      WO98/10097 A2      3/1998

(Continued)

OTHER PUBLICATIONS

Ambrose et al., Detection and spectroscopy of single pentacene molecules in a *p*-terphenyl crystal by means of fluorescence excitation. J Chem Phys. Nov. 15, 1991;95(10):7150-63.

(Continued)

*Primary Examiner*—Michael Stafira
(74) *Attorney, Agent, or Firm*—Wolf, Greenfield & Sacks, P.C.

(57) ABSTRACT

The invention relates to methods and systems for detecting and or analyzing an agent in a sample with a chip having optical components incorporated therein.

20 Claims, 4 Drawing Sheets

U.S. PATENT DOCUMENTS

| | | |
|---|---|---|
| 2002/0187508 A1 | 12/2002 | Wong |
| 2002/0197639 A1 | 12/2002 | Shia et al. |
| 2003/0059822 A1 | 3/2003 | Chan et al. |
| 2003/0215864 A1 | 11/2003 | Gilmanshin et al. |
| 2003/0235854 A1 | 12/2003 | Chan |
| 2004/0009612 A1 | 1/2004 | Zhao et al. |
| 2004/0053399 A1 | 3/2004 | Gilmanshin |
| 2004/0166025 A1 | 8/2004 | Chan et al. |
| 2004/0214211 A1 | 10/2004 | Gilmanshin et al. |
| 2004/0235014 A1 | 11/2004 | Nadel et al. |
| 2005/0042665 A1 | 2/2005 | Gilmanshin |
| 2005/0112595 A1 | 5/2005 | Zhao et al. |
| 2005/0112606 A1 | 5/2005 | Fuchs et al. |
| 2005/0112620 A1 | 5/2005 | Chan |
| 2005/0112671 A1 | 5/2005 | Maletta et al. |
| 2005/0123944 A1 | 6/2005 | Neely et al. |
| 2005/0123974 A1 | 6/2005 | Gilmanshin et al. |
| 2005/0142595 A1 | 6/2005 | Maletta et al. |
| 2005/0153354 A1 | 7/2005 | Gilmanshin et al. |
| 2005/0196790 A1 | 9/2005 | Rooke et al. |
| 2005/0221408 A1 | 10/2005 | Nalefski et al. |
| 2006/0078915 A1 | 4/2006 | Fuchs et al. |
| 2006/0134679 A1 | 6/2006 | Larson et al. |
| 2006/0160209 A1 | 7/2006 | Larson et al. |
| 2006/0160231 A1 | 7/2006 | Nadel et al. |

FOREIGN PATENT DOCUMENTS

| | | |
|---|---|---|
| WO | WO 00/09757 A1 | 2/2000 |

OTHER PUBLICATIONS

Fleury et al., Fluorescence spectra of single pentacene molecules in *p*-terphenyl at 1.7 K. Chem Phys Letts. 1995; 236:87-95.

Nie et al., Probing individual molecules with confocal fluorescence microscopy. Science. Nov. 11, 1994;266(5187):1018-21.

Orrit et al., Single pentacene molecules detected by fluorescence excitation in a p-terphenyl crystal. Phys Rev Lett. Nov. 19, 1990;65(21):2716-2719.

Shera et al., Detection of single fluorescent molecules. Chem Phys Letts. 1990; 174(6): 553-7.

Tamarat et al., Ten years of single-molecule spectroscopy. J Phys Chem. 2000; 104(1):1-16.

[No Author Listed] "Manual>>Principles." FACS Facility Online. http://citometria.germanstrias.org/eng/principles.htm. 3 pages. Updated Aug. 28, 2000.

[No Author Listed] "FLP Series Lenses for Luxeon LEDs: Luxeon I, III, and V, Star and Emitter." Fraen Srl Maximizing Light Online. http://www.fraensrl.com/images/FLP_Lens_Series_Datasheet. pdf. 8 pages. Jan. 4, 2005.

Castro et al., Single-Molecule Electrophoreses: Applications to Biomolecular Detection. SPIE. 1995; 2396:79-85.

Ekstrøm et al., Two-point fluorescence detection and automated fraction collection applied to constant denaturant capillary electrophoresis. Biotechniques. Sep. 2000;29(3):582-4, 586-9.

Roulet et al., Fabrication of multilayer systems combining microfluidic and mirooptical elements for fluorescence detection. J Micro Systms. Dec. 2001;10(4):482-91.

Roulet et al., Performance of an integrated microoptical system for fluorescence detection in microfluidic systems. Anal Chem. Jul. 15, 2002;74(14):3400-7.

Shortreed et al., High-throughput single-molecule DNA screening based on electrophoresis. Anal Chem. Jul. 1, 2000;72(13):2879-85.

\* cited by examiner

SYSTEMS AND METHODS FOR MEASUREMENT OPTIMIZATION

RELATED APPLICATIONS

This application claims priority to U.S. Provisional Applications Serial No. 60/618,453 entitled "Measurement Optimization Using Microlens" filed Oct. 13, 2004, the entire contents of which are incorporated by reference herein.

GOVERNMENT SUPPORT

This invention was made in part with government support under Contract No. W81XWH-04-9-0011 from the Homeland Security Advanced Research Projects Agency. The Government may retain certain rights in the invention.

FIELD OF THE INVENTION

The invention relates in part to a chip incorporating a microfluidic channel and a lens used to detect contents of the channel.

BACKGROUND OF THE INVENTION

Systems are known that utilize chips to receive a sample for optical inspection to determine whether an agent is present in the sample. The agents often include polymers, such as nucleic acids with detachably labeled probes bound thereto in a particular manner. The sample is passed through a detection zone where an excitation signal illuminates the probe. The labels of the probe are excited when present in the detection zone and emit an emission signal. The emission signal is received by a collector that is separate from the chip and that, in turn, directs the emission signal to a detector as a portion of a detection signal. The characteristics of the emission signal relative to the sample, the excitation signal, the surroundings, and/or other characteristics are then used by the system to detect the presence of the polymer and/or to analyze structure of the polymer.

Alignment between optical components and chips of prior art systems can be critical to the reliability of the system and the quality of information produced by the system. Emitters and/or collectors are often required to be focused into a small detection zone so that the position of a probe associated with a polymer can be determined with precision when present in the detection zone. Expensive, adjustable focus lenses are used in prior art systems to accommodate variations in the positional relationship between a chip used by the system and optical components that are separate from the chip. Costly motion control systems are also used in prior art systems to maintain the positional relationship between optical components and/or to minimize the impact of movement, such as vibrations in the system. There exists a need in the art for a system that minimizes the costs associated with positioning a chip relative to optical detection components and is less (if at all) sensitive to vibrations.

Prior art detection systems can have difficulty distinguishing emission signals from noise and/or disturbances within the system. This may be the case particularly in systems that attempt to detect a single polymer or molecule. Noise and/or disturbances may emanate from any number of sources, including emission signals that are overlapped with excitation signals in the system prior to being received by a detector. To this end, there also exists a need for detection and analysis systems that minimize or prevent the overlap of emission and excitation signals. There is also a need to increase the proportion of a signal received from each agent relative to background noise, transmitted illumination, and/or path fluorescence, particularly for single molecule detection. Compound lenses with relatively high numerical apertures are used in prior art systems to increase the proportion of signals received from any given agent. However, such compound lenses are often expensive and require significant amounts of space within a system. This prevents such high numerical aperture lenses from being incorporated in many detection systems, particularly where multiple detection zones are desired. Consequently, there is a need in the art for high numerical lens capable of being incorporated into a system with smaller spatial requirements and at a lower cost.

Expensive and space consuming lenses preclude the utilization of multiple detection zones on a single chip in prior art systems. In this regard, the amount of information that can be obtained from a sample in a given amount of time (i.e., throughput) can be limited in prior art systems. There is a need to reduce the cost and size of optical components in detection systems such that higher throughput, parallel processing of samples on a chip can be achieved in a cost effective manner.

SUMMARY OF THE INVENTION

The invention provides, in its broadest sense, a system capable of rapid and reliable detection and/or analysis of agents, such as biohazardous agents. The system combines various technologies, including microfluidics and single molecule detection capability. In some embodiments, microfluidic channels and optics are incorporated directly into a chip, such that the optics can be produced in-focus and at a lower cost. Incorporating optics directly into a chip can reduce the impact that vibrations have on the reliability of information produced by the system. Incorporating optics into the chip can also allow numerous detection zones to be placed into a single chip, thus increasing the amount of information that can be derived from a sample in the chip during a given time frame.

In one aspect, the invention provides a chip for use in detecting an agent. The chip comprises a microfluidic channel incorporated into the chip. The microfluidic channel is adapted to deliver a fluid that may contain an agent to a detection zone that lies at least partially in the channel. An illuminator is incorporated into the chip and is adapted to direct an excitation signal to the detection zone. A concave reflector is incorporated into the chip and has a focal point at the detection zone. The concave reflector is constructed and arranged to receive an emission signal from the agent when present in the detection zone and to reflect the emissions signal to a detector.

In one aspect, the invention provides a chip for use in detecting an agent. The chip comprises a microfluidic channel incorporated into the chip. The microfluidic channel is adapted to deliver a fluid that may contain an agent to a detection zone that lies at least partially in the channel. The chip also comprises a concave reflector incorporated into the chip in fixed relationship with respect to the channel. The reflector has a focal point at the detection zone and the concave reflector is constructed and arranged to receive an emission signal from the agent when present in the detection zone and to reflect the emission signal to a detector.

The invention further provides a method that comprises providing a chip as described herein. The method also comprises providing a fluid that may contain the agent to the channel and illuminating the detection zone with the excitation signal to cause any agent present in the detection zone to emit an emission signal. The method further comprises receiving the emission signal with the concave reflector and reflecting the emission signal toward the detector to determine whether the agent is present in the detection zone.

In still another aspect, the invention provides a chip for use in detecting an agent. The chip comprises a microfluidic channel incorporated into the chip. The microfluidic channel is adapted to deliver a fluid containing an agent to a plurality of detection zones that each lie at least partially in the channel. A plurality of concave reflectors are incorporated into the chip and are each held in a fixed relationship with respect to one of the plurality of detection zones. A plurality of illuminators are incorporated into the chip, each of the plurality of illuminators are adapted to provide an excitation signal to one of the plurality of detection zones.

Various embodiments apply equally to the various aspects of the invention and for the sake of convenience these are recited once below.

In one embodiment, the chip includes a plurality of concave reflectors and illuminators each associated with one of a plurality of detection zones at the channel. In one embodiment, fluid is provided that may contain the agent comprises providing the fluid to each of the plurality of detection zones.

In one embodiment, the concave reflector is incorporated into the chip in a fixed relationship with respect to the channel.

In another embodiment, a solid medium provides a pathway from the microfluidic channel to the concave reflector along which the emission signal can travel without substantial refraction. In one embodiment, the solid medium extends from a wall of the channel to the concave reflector. Still, in one embodiment, a cover slip is adapted to mate with the chip to enclose the channel and the concave reflector is incorporated into the cover slip. In still another embodiment, the solid medium provides a pathway from the microfluidic channel to the illuminator along which the excitation signal can travel without substantial refraction.

In one embodiment, the illuminator and the concave reflector are on opposed sides of the channel. In one embodiment, the illuminator is a refractive illuminator having a focal point substantially located at the focal point of the concave reflector. In another embodiment, the illuminator is a reflective illuminator having a focal point substantially located at the focal point of the concave reflector. In still another embodiment, the concave reflector includes an aperture positioned to allow the excitation signal to pass therethrough to prevent the excitation signal from being reflected toward the detector. In yet a further embodiment, the concave reflector is constructed and arranged to reflect at least a portion of the excitation signal.

One embodiment includes a wavelength specific filter positioned to receive the emission signal and the excitation signal from the concave reflector. The wavelength specific filter is adapted to direct at least a portion of the emission signal to the detector and to prevent the excitation signal from reaching the detector. In some embodiments, a second reflector is constructed and arranged to receive and reflect the emission signal to the detector while allowing the excitation signal to pass thereby.

In one embodiment, the illuminator includes a refractive illuminator having a focal point substantially located at the focal point of the concave reflector and the illuminator and the concave reflector are positioned on a common side of the channel. In one of such embodiments, the illuminator and the concave reflector are constructed and arranged such that overlap of the excitation signal and the emission signal is minimized. The concave reflector can include a central aperture. The refractive illuminator can be positioned at the central aperture. The embodiment can include a second reflector constructed and arranged to reflect the excitation signal back through the aperture and toward the refractive illuminator. The second reflector can be substantially located at the focal point of the concave reflector.

In some embodiments, the concave reflector has a collection half angle greater than 50 degrees, greater than 65 degrees, or greater than 85 degrees. In some embodiments, the reflector has a numerical aperture of 1.0 or greater, or of 1.3 or greater.

In one embodiment, the reflector is a parabolic reflector. In one embodiment, the illuminator includes a waveguide incorporated into the chip. In one embodiment, a waveguide can be constructed and arranged to illuminate the microfluidic channel with an evanescent excitation signal.

In some embodiments, the chip comprises a plurality of pairs of concave reflectors and illuminators, each pair associated with a corresponding detection zone. The chip can comprise more than 50 pairs of concave reflectors and illuminators. The plurality of pairs of concave reflectors and illuminators can be arranged in serial along a common channel. The chip can also comprise a plurality of channels, with the plurality of pairs of concave reflectors and illuminators arranged about the plurality of channels.

In some embodiments, the detection zone is circular in shape. The detection zone can have a diameter of about 1.7 microns. The detection zone can be elliptical in shape, and can have a minor diameter of about 1.7 microns. In some embodiments, the detection zone extends beyond the channel.

In some embodiments, the agent comprises a plurality of agents. The agent can be a polymer. The polymer can be a nucleic acid optionally selected from the group consisting of DNA or RNA. The polymer can be a peptide including a protein. The agent can also be a cell or a pathogen.

These and other aspects of the invention, as well as various advantages and utilities, will be more apparent with reference to the detailed description of the preferred embodiments and to the accompanying drawings.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

The phraseology and terminology used herein is for the purpose of description and should not be regarded as limiting. The use herein of "including", "comprising", "having", "containing", "involving", and variations thereof, is meant to encompass the items listed thereafter and equivalents thereof as well as additional items.

BRIEF DESCRIPTION OF THE FIGURES

The accompanying Figures are not intended to be drawn to scale. For purposes of clarity, not every component may be labeled in every Figure.

Figure 1:
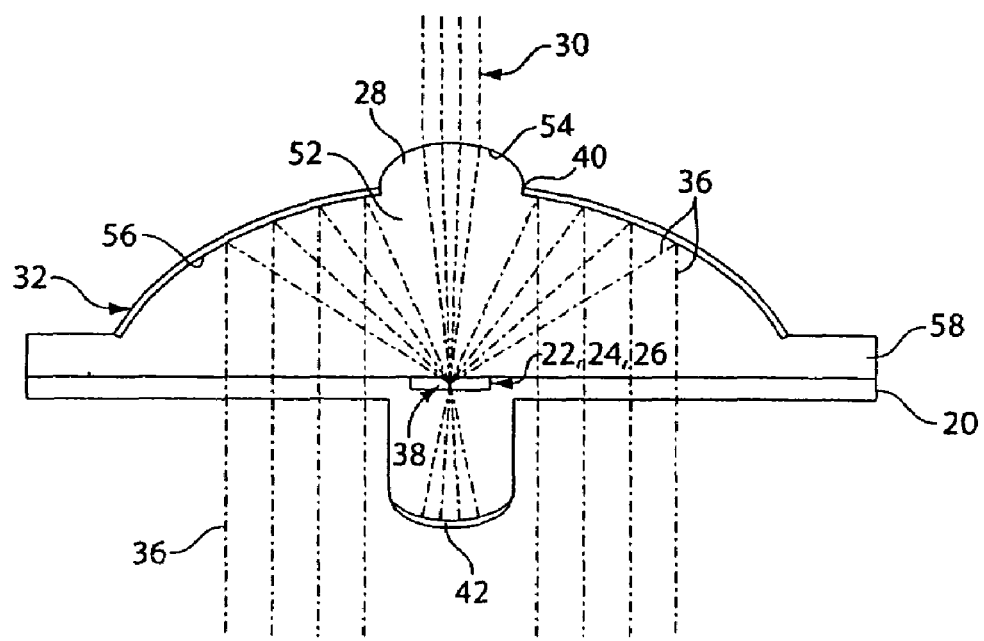
FIG. 1 is a cross sectional view of optical components incorporated into a chip.

It is to be understood that the Figures are not required for enablement of the invention.

Other aspects, embodiments and features of the invention will become apparent from the following detailed description of the invention when considered in conjunction with the accompanying Figures.

All patent applications and patents cited herein incorporated by reference in their entirety. In case of conflict, the present specification, including definitions, will control.

DETAILED DESCRIPTION OF THE INVENTION

The invention provides systems and methods for detecting whether an agent is present in a sample. The systems and method generally use chips having microfluidic channels incorporated therein. Optical components are incorporated into the chip to provide various benefits over prior art systems with components that are separate from the chip. In some embodiments, one or more reflectors and/or illuminators are incorporated into the chip during manufacturing to reduce overall system cost. Incorporating illuminators and/or reflectors into the chip can eliminate the need for costly optical components in the system—like adjustable objective lenses. Moreover, incorporating optical components into the chip can make the system less susceptible to vibrations and/or provide a chip that is manufactured in focus. The optical components can be arranged to maximize their numerical aperture and thus improve the signal to noise ratio of emissions received by the system. Still, in some embodiments overlap between the excitation and emissions signal is minimized to increase the signal to noise ratio. Optical components can also be incorporated into the chip in arrays to increase the amount of information derived from a given sample as the sample passes through channels in the chip.

As used herein, the term "emission signal" denotes emissions of an agent in the detection zone, such as the fluorescent emissions of some labels that may be incorporated into an agent. The term "detection signal" is used to denote an entire signal received from the detection zone of a system, regardless of how many emission signals it may contain and/or the amount and type of noise or disturbances that it may also contain. In this manner, the detection zone and its contents define the detection signal. As used herein, the term "excitation signal" is used to describe the emissions of an emitter that may be used to excite a label. As used herein, the term "detection zone" is used to denote the zone that is illuminated at a chip by an excitation signal in the system. In some embodiments, the detection zone has a circular cross section across at the fluidic channel and is further defined by the intersection of a circular illumination field and the channel. The circular detection zone can have a diameter of 1.7 microns. The detection zone can be an elliptical section across the fluidic channel defined by the intersection of an elliptical illumination field and the channel, or can extend beyond the channel. The elliptical detection zone can have minor axes of 1.7 microns. In some embodiments, the detection zone is defined by the reach of an evanescent excitation signal that impinges upon a microfluidic channel.

As used herein, the term "collector" denotes an optical component that receives and re-directs optical signals from a detection zone. In many embodiments, the collector includes a concave reflector with a focal point at the detection zone. The collector has a parabolic shape in some embodiments, but can have different shapes to suit different applications. In some embodiments, the shape of the collector is adjusted to accommodate refraction that may occur to signals between the detection zone and the collector.

As used herein, the term "illuminator" denotes an optical component that directs an excitation signal to a detection zone. In some embodiments, the illuminator is a refractive illuminator with a curved surface that receives an excitation signal from an emitter like a laser source and focuses the excitation signal to a focal point. In other embodiments, the illuminator comprises a concave, reflective surface that focuses an excitation signal to a focal point. A waveguide incorporated into the chip is one example of such an illuminator.

Turn now to FIG. 1, which shows optical components incorporated into a chip 20 according to one embodiment. The chip includes a microfluidic channel 22 adapted to receive a sample 24 comprising a carrier fluid that may contain an agent 26. An illuminator 28 is positioned on one side of the channel to receive an excitation signal 30 from the system and to focus the excitation signal at the channel. A concave, reflective collector 32 is positioned to have a focal point that lies at the channel, coincident with the focal point of the illuminator. The collector receives a detection signal from the detection zone and reflects the detection signal toward a downstream detector 34 (not shown) for analysis. The detection signal includes emission signals 36 from any agents that are illuminated by the excitation signal when passing through the detection zone 38.

FIG. 1 also illustrates the path followed by the excitation and emission signals through the optical components of the chip, according to one embodiment of the invention. The refractive illuminator receives an excitation signal from an emitter and focuses the excitation signal through an aperture 40 in the collector to a focal point at the channel. The focused excitation signal defines a detection zone at the channel. A concave mirror 42 positioned on the opposite side of the chip reflects the excitation signal at a lower irradiance back through the chip and through the aperture. In another embodiment, the mirror reflects the excitation signal transversely out of the chip. Agents or other excitable components present in the detection zone emit emission signals when illuminated by the excitation signal. A concave reflector, having a focal point coincident with the focal point of the illuminator, receives a detection signal from the detection zone that includes the emission signals from any agents in the detection zone. Either directly or indirectly via intermediate optical components 44 (not shown) such as mirrors and/or filters, the detection signal is then reflected by the collector toward a downstream detector.

Figure 2:
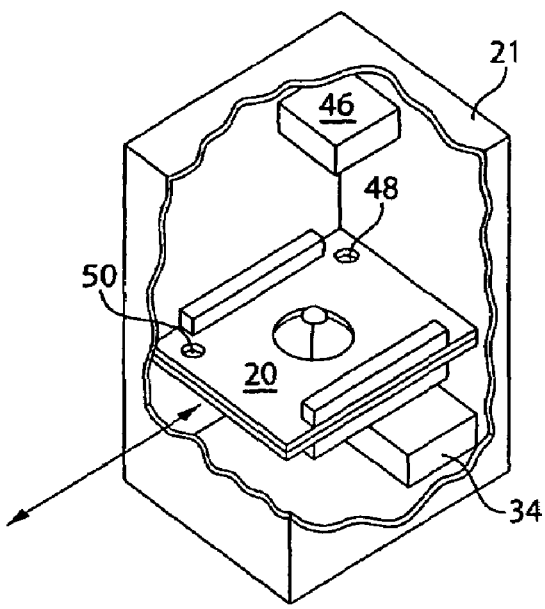
FIG. 2 is a schematic view of components commonly found in systems that mate with chips of the present invention.

FIG. 2 shows components found in many systems 21 that may interface with chips of the present invention. The illustrated system includes a plurality of emitters 46, such as lasers, to create excitation signals that are directed toward the illuminators of the chip. The system also includes a plurality of detectors 34 that receive detection signals from the chip. The detectors convert detection signals into electronic signals that are analyzed by downstream data processors. The data processors determine the presence and/or structure of agents in samples provided to the chip. Some examples of detectors that may be used in detection systems include avalanche photo diodes, and channel photomultiplier tubes. The illustrated detection system includes a sample introduction port 48 that receives a sample to be delivered to the microfluidic channel of the chip. The sample is moved through plumbing in the system and into a port on the chip by a pump or through electrokinetics. Once received in the port, the sample is delivered through the channels in the chip and through detection zones positioned at points of the channels. The sample is then delivered through an exit port 50 of the chip and into a waste collection reservoir of the system.

In one embodiment, a field mirror is used to increase the illumination at the detection zone. The excitation signal is reflected off of the mirror and back through the detection zone toward the illuminator. In this sense, the excitation signal passes through the detection zone twice, increasing the illumination at the detection zone by a factor of two. It is to be appreciated that not all embodiments of the invention include field mirrors, and those that do include a field mirror are not required to reflect light back toward the illuminator. In some embodiments, the field mirror comprises a flat surface formed of gold that is embedded into the chip. In some embodiments, the mirror is incorporated directly into the chip at the bottom of the channel. In other embodiments, the field mirror comprises a reflective ellipsoidal surface embedded into the chip. Some embodiments may have a field mirror or a prism that directs the excitation signal out of the chip in a transverse direction, rather than back toward the illuminator. Still, in other embodiments, the excitation signal may pass through the chip from one side to another without being reflected, as aspects of the invention do not require a field mirror. In other embodiments, a beam dump is placed adjacent to the chip, or is incorporated into the chip to receive the excitation signal after it has passed through the chip.

In one embodiment of FIG. 1, the collector includes a central aperture that receives the illuminator. The aperture is positioned in the collector to allow transmission of the excitation signal to the detection zone. The aperture of the collector may also allow exit of the illumination in direction away from the detector. Portions of emission signals directed toward the aperture will not be reflected toward the detector. However, the loss of such emission signals can be offset by elimination of the excitation signal from the detection signal. Although the aperture in FIG. 1 is located centrally within the reflector, it can be located elsewhere in other embodiments. By way of example, the aperture can be positioned on a side of the reflector. In other embodiments, the collector may lack an aperture altogether, as aspects of the invention are not limited in this respect.

The collector, illuminator, and aperture of FIG. 1 are constructed and arranged to prevent portions of the detection signal that have been overlapped with the excitation signal from being received by the collector. As is shown by the signal tracings in FIG. 1, the excitation signal reaches the detection zone without crossing the path of any emission signals that are eventually directed toward a detector in the system. In this sense, overlap between the excitation and emission signals is avoided, which can decrease the signal to noise ratio of the system by increasing background fluorescence in the detection signal. Some overlap between the excitation signal and the emission signal may occur directly above the detection zone. However these portions of the emission signals are not likely to pose problems as they typically will not be reflected by the collector but rather allowed to pass through the aperture in the collector and out of the chip. It is to be appreciated that not all embodiments of the invention minimize overlap between excitation and emission signals, and that overlap is acceptable in some embodiments. For instance, the excitation signal, once reflected by the concave mirror 42, has less irradiance and should not adversely affect the emission signals if overlap occurs.

The excitation signal can be utilized by the system to determine when the chip is in proper alignment. By way of example, in one embodiment of FIG. 1, the field mirror is sized and positioned to reflect the excitation signal through the central aperture in the collector only once the excitation signal is in position at the channel. In some embodiments, the bottom of the channel may serve to reflect the excitation signal itself, or may include a reflective coating or mirror to help accomplish this effect. The system includes a detector that receives the excitation signal after it is reflected from the mirror to indicate that the chip is positioned properly. In other embodiments, the field mirror or a prism may direct the excitation signal toward a detector in a different direction, such as transversely out of the chip, to determine proper positioning. Still, some embodiments may lack a field mirror that reflects the excitation signal. In such systems, a detector can be placed on a side of the chip that is opposed to the illuminator, such that the excitation passes through the aperture, across the chip and into a detector when the chip is positioned properly. Still, other embodiments can have other features to indicate proper positioning of the chip. Some features include switches that contact portions of the chip to indicate proper position, as aspects of the present invention are not limited to any one particular mode of determining proper chip positioning, and some embodiments completely lack such a capability.

Embodiments of the invention are constructed to minimize unwanted refraction of emission and/or excitation signals that pass through the chip. As shown FIG. 1, the medium 52 that lies between the channel and the collector comprises a solid, continuous medium such that light passing there between does not cross any boundaries where substantial refraction can occur. As used herein, "substantial refraction" refers to refraction associated with a particular boundary that causes a decrease in the numerical aperture of an optical device by 5% or more. The "collector numerical aperture" for collectors is defined by a collection ray bundle that includes the detection zone, the margin of the collector, and the detector. The "illuminator numerical aperture" for illuminators is defined by an illumination ray bundle that includes the emitter, the margin of the illuminator, and the detection zone. Similarly, the medium that lies between the illuminator and the channel can be a solid, continuous medium. Such a solid, continuous medium can prevent substantial refraction of light passing there through. In one embodiment of FIG. 1, the cover slip and the medium that lies between the upper boundary of the channel, the collector and the illuminator comprises a monolithic piece of CORN- ING 550. CORNING 550 is favorable in some embodiments as it can be molded; however, other embodiments can use different materials, as aspects of the invention are not limited to any one type of material.

Optical components can be incorporated into the boundary of the solid medium to further prevent unwanted refraction. For instance, the illuminator in the embodiment of FIG. 1 comprises a surface at the boundary 54 of the solid medium. It is shaped to refract an excitation signal to the focal point at the channel. No further substantial refraction occurs until the excitation signal exits the cover slip at the channel boundary. The collector in the embodiment of FIG. 1 comprises a coating of metal such as aluminum or silver with a protective coating that is applied to the outer surface 56 of the medium to maximize reflectance.

The illuminator and collector of the embodiment in FIG. 1 are incorporated into the chip by virtue of being part of the solid medium 52 that includes the cover slip 58 of the chip. However, the optical components or other features can be incorporated into a chip in different manners. As used herein, the phrase "incorporated into a chip" refers to a component that is held to the chip in a way that causes the component to move together with the chip. In this sense, when a chip is moved or subjected to vibration, each component that is incorporated into the chip is subjected to the same movement or vibration. In this regard, critical alignments between components that are incorporated into a chip are less susceptible to problems associated with chip movement or chip/system vibrations.

As mentioned herein, relationships that are critical to satisfactory operation of a system, such as the relationship between an illuminator and/or collector and a channel of a chip, can be made more robust by incorporating the optical components into the chip. For example, the position of the detection zone relative to the channel (as defined by either the illuminator or the collector) can be critical in determining whether an agent is present in the detection zone. If the detection zone is moved to allow agents to pass through the channel without entering the detection zone, the system may register a false negative reading. Similarly, if the detection zone is positioned differently than expected, labels that are bound to polymers (e.g., via a probe) may be interpreted to be at incorrect positions on the polymer, and thus lead to an incorrect interpretation of the polymer structure, including polymer sequence. As mentioned herein, incorporating the illuminator and/or collector into the chip allows the detection zone to be held at a fixed position relative to the channel, thus preventing problems associated with improper detection zone location.

The interface between the illuminator on the chip and the emitter in the system can be sensitive to angular alignment. Due to infinitely distant conjugates, the interface between the illuminator on the chip and the emitter in the system can be insensitive to spatial alignment. Therefore, the entire system may expand or contract without significant degradation to the interface between the illuminator on the chip and an emitter as long as angular orientations are preserved. During manufacture, the interface between the illuminator and the channel can be sensitive to spatial alignment. During manufacture, the interface between the illuminator on chip and the emitter can be sensitive to angular alignment. The emitter in the system can direct an excitation signal that is larger in cross section than the exposed surface of the illuminator. In some embodiments, the illuminator will be nominally positioned in the center of the laser so that if movement occurs, the illuminator may still be located entirely within the laser. The areas surrounding the illuminator on the chip can be opaque or reflective, so that the excess excitation signal does not enter the chip. In some embodiments, the excitation signal comprises an area that is 50% greater than the cross sectional area of the illuminator. In other embodiments, the excitation signal comprises an area that is more than 100% greater than the cross sectional area of the illuminator, or even more than 200% times greater than the cross sectional area of the illuminator. In such embodiments, the system can still operate even if the illuminator is only partially bathed in the excitation signal. Here, the illuminator will still create a detection zone at the appropriate spot, but at a lower intensity. In other embodiments where the excitation signal has the same or smaller cross sectional area as the illuminator, movement of the excitation signal about the surface of the illuminator will have little effect on the overall position of the detection zone but may affect the intensity at portions of the detection zone.

For reasons similar to those discussed herein with respect to the illuminator, the interface between the collector on the chip and the detector in the system (or an intermediate optical component in the system, such as a mirror or filter) can be made robust to movement. In many embodiments, the surface of the detector or mirror that receives the detection signal directly from the chip has an area larger than the detection signal that it is intended to receive. The larger area of the collector or mirror can receive the detection signal even if there is misalignment between the elements. This is yet another way in which incorporating optical components into the chip can reduce a system's susceptibility to vibrations.

Components that are incorporated into the chip can be physically inseparable from the chip or a cover slip. For instance, in some embodiments one monolithic piece of material forms the chip, the collector and the illuminator. In such embodiments, the collector and illuminator can be present on one side of the chip and the channel can be exposed on the opposite or the opposed side of the chip that receives a cover slip. In other embodiments, components are incorporated into a chip, but can be separated there from. By way of example, in the embodiment of FIG. 1, the illuminator and collector are incorporated into the chip by virtue of being formed into the cover slip that mates with the chip.

Figure 3:
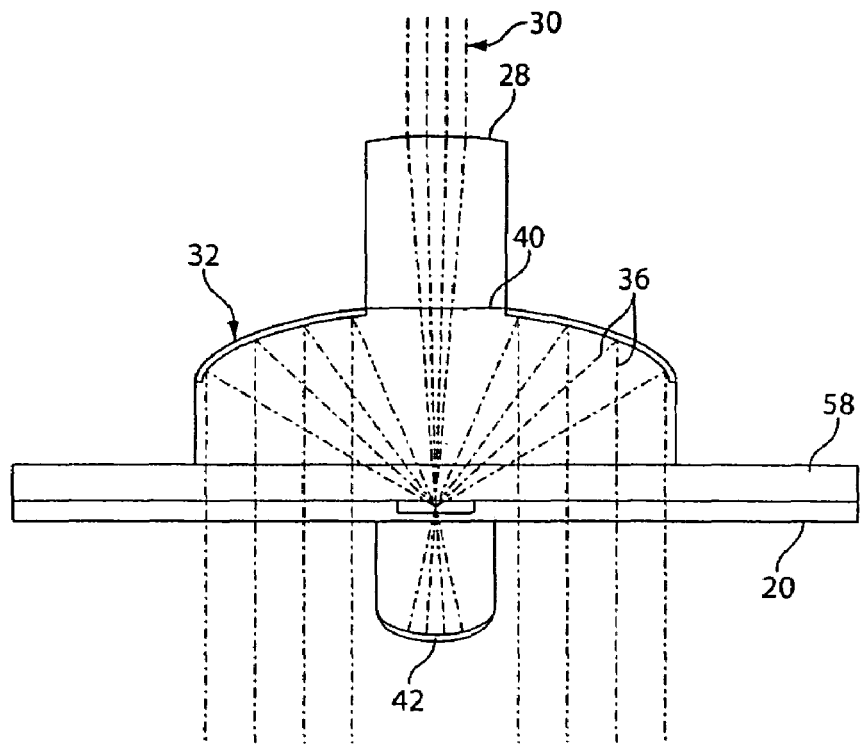
FIG. 3 is a cross sectional view of a chip formed of separable optical components that are incorporated into a chip.

In still other embodiments, the components that are incorporated into the chip can be separable from the chip or cover slip. FIG. 3 shows an example of a separable cover slip, a separable collector and a separable illuminator that are incorporated into a chip. The chip includes a microfluidic channel that receives and passes a sample that may contain an agent through a detection zone in the channel. A cover slip is mated to the chip so that a lower surface of the slip provides an upper boundary 60 to the channel, thereby enclosing the channel. A concave, reflective collector is mated to the upper surface of the cover slip and such that, when assembled, the focal point of the collector is at the channel. The collector includes a central aperture 40 in which a separate, refractive illuminator is positioned. The illuminator is mated to the aperture in the collector such that the focal point of the illuminator is also positioned at the channel and coincident with the focal point of the collector.

Separable components incorporated into a chip, like that of FIG. 3, can be mated together in various ways. By way of example, the collector shown in FIG. 3 includes a separate chip, cover slip, collector, illuminator and mirror that are incorporated into the chip. In some embodiments the optical components may need to be aligned precisely as they are incorporated into the chip. For instance, the illuminator may require close assembly tolerances for proper alignment of the detection zone at the channel. To accommodate such assembly tolerances, in one embodiment, the thickness of the illuminator is varied to improve the focus of a collimated beam (i.e., the excitation signal) at the channel. Here, the illuminator thickness may be varied with an adhesive filling the gaps at the interface between the illuminator of the collector or the illuminator may be ground to the optimum length for focus of the excitation signal. In one embodiment, the lateral position of the illuminator is directed orthogonally onto the channel. During assembly, the lateral position of the illuminator can be actively aligned and then fixed in place. Alignment may include positioning the illuminator to satisfy an acceptable angular error between the emitter and the illuminator.

Some embodiments with separable optical components include registration features to aid in alignment during assembly. In one embodiment, the collector receives the illuminator in only a single location that positions the illuminator and collector to have coincident focal points. In another embodiment, the chip, cover slip, and or collector can have recessed portions adapted to receive and position mating components. Other components of the chip can have similar or different types of location aids, such as patterns on the chip, like a circle or square that mates with another component, as aspects of the present invention are not limited in this regard. Registration features can be included that position any of the components relative to one another. By way of non-limiting example, posts may extend from the chip, through a cover slip and into a collector to directly register the collector with respect to the chip. Still, other registration features are possible, as aspects of the invention are not limited in this regard.

In embodiments that include separable components that are incorporated into a chip, like the embodiment of FIG. 3, the interface between separate optical components can be arranged to minimize the reflection of light. This allows collection of light near and beyond the critical angle for total internal reflection. By way of example, the interface between the collector and the cover slip or the collector and the illuminator of FIG. 3 can include a thin layer of immersion oil to reduce the reflection of light crossing the interface. In other embodiments, the interface includes a thin adhesive that holds the components relative to one another and reduces the reflection of light crossing the interface.

Aspects of the present invention also facilitate collectors that maximize the amount of emission signals received by the collector. This can prove particularly beneficial in systems that are used to detect single molecules. Collection efficiency is frequently quantified by a numerical aperture for a given lens, which is defined by Eq. 1 below and illustrated in FIG. 1.

$$NA = n \sin \theta \qquad \text{Eq. 1}$$

where:
NA=Numerical Aperture
n=Refractive index of the medium in which the collector operates
θ=Half angle between the collector and the channel Numerical aperture can be maximized by increasing the half angle of the collector. Incorporating the collector into the chip allows the collector margin to be moved closer to the microfluidic channel. A collector margin that lies closer to the channel can surround the channel to a greater degree than a collector that is further away from the channel. In this manner, moving the collector margin closer to the channel can increase the half angle of collection and thus the numerical aperture of the collector. Embodiments of the present invention have half angles up to 50 degrees, 75 degrees, 85 degrees and even up to 90 degrees. A monolithic solid from the channel to the collector can have a half angle of 90 degrees. In other embodiments, numerical apertures normally achieved with a 90 degree half angle can be achieved by index matching of components that lie on the path between the channel and the reflector. In some embodiments, the reflector/collector has a numerical aperture of 1.0 or greater, 1.3 or greater, or 1.5 or greater. These numerical apertures correspond to half angles of 39 degrees, 55 degrees, and 69 degrees, respectively within glass having a refractive index of 1.60, such as CORNING 550. Half angles of 49 degrees, 78 degrees, and 90 degrees will produce similar numerical apertures, respectively, in water, which has an index of 1.33. It is to be understood that the half angle is measured along the central axis of the collector although the central portion of collectors that include apertures do not effectively collect emissions. In this respect, Eq. 1 provides numerical aperture values, as recited in the specification or the claims, that are not corrected for apertures within the collector. Under this current definition of numerical aperture, the collection efficiency increase monotonically with numerical aperture.

Illuminators and collectors can be manufactured specifically to the application for a given chip to reduce overall system costs. As is to be appreciated, compound lenses found in prior art systems are frequently designed to accommodate a large spatial field and different wavelengths of light. These requirements introduce complexities into the lens that increase cost. Incorporating optical components, such as collectors or illuminators, into a chip allows the components to be designed with only a small field, thus reducing the number of lenses and other required components. Similarly, the optical components incorporated into a chip may only need to accommodate a narrow range of wavelengths (i.e., the wavelengths associated with excitation and emission signals that are to be used in combination with the chip). Here, the illuminator can operate at essentially a single wavelength, thus reducing or eliminating chromatic aberrations in the illuminator. The collector can operate in a reflective mode with no chromatic aberrations due to reflection. Each element performs a specific task with a minimum complexity. Lower cost materials may be available, such as some plastics, that can accommodate wavelengths of excitation and emission signals, while not necessarily accommodating others.

$$A\Omega = \lambda^2 \qquad \text{Eq. 2}$$

The Etendue or space-angle product for Gaussian profile beam is defined by Eq. 2 above, in which A is the area of the spot, Ω is the solid angle of divergence, and λ is the wavelength. A Gaussian beam creates the smallest space-angle possible. It can be preferred over the larger space-angle products due to a circular or rectangular geometry. The planar version of the space-angle product can be defined below by Eq. 3 in which d is the linear dimension of the spot, and β is the full plane-angle of divergence.

$$d\beta = \frac{4}{\pi}\lambda \qquad \text{Eq. 3}$$

The size of the illumination field is determined by the wavelength of excitation and the numerical aperture of the illuminator. For a circular spot, the diameter of the illumination field is defined by Eq. 4 below.

$$d_{IF} = 1.27 \frac{\lambda}{2NA} = 0.63 \frac{\lambda}{n \sin \theta} \qquad \text{Eq. 4}$$

An illumination field of 1.7 microns in width should have an NA 0.18 for an excitation wavelength of 488 nm. The half-angle within water should be 7.8 degrees. The half-angle within glass of index 1.5 should be 13.5 degrees. The depth of focus is determined by a doubling of the spot area at which point the peak irradiance is cut in half and the diameter is scaled by 1.4. The depth of focus in channel for circular spot is defined by Eq. 5 below, where $\lambda_C$ is the wavelength in the channel, $\Omega_C$ is the solid angle in the channel, $n_C$ is the refractive index of the channel, $\lambda_0$ is the wavelength within air.

$$\Delta z_{IF} = \frac{\lambda_C}{\Omega_C} \approx \frac{n_C \lambda_0}{\pi NA^2} \qquad \text{Eq. 5}$$

For a circular spot within water, the depth of focus is ±05.8 um. An elliptical spot may be created by an elliptical beam at the illuminator aperture. Its width and depth of focus are the same as the circular spot. However, over the same depth of focus for a circular spot, the peak intensity is not cut in half. The peak intensity of the elliptical spot is scaled by 0.71 over the depth of focus. Therefore and elliptical beam at the aperture of the illuminator may be advantageous due to a smaller drop in irradiance throughout the depth of focus.

The size and shape of the detection zone can be tailored by the design of the illuminator and/or reflector. In many embodiments, particularly those suited for single molecule detection, it is desirable for the detection zone to extend entirely across the channel in a direction perpendicular to flow. This can prevent an agent from passing by the detection zone without being excited by the excitation signal. It can also be desirable to minimize the length of the detection zone in a direction parallel to flow in the channel. Many systems cannot determine the precise location of an agent within a detection zone, but rather can simply detect whether the agent is present. In this regard, detection zones that extend further in a direction parallel to flow can produce results with less precision. To this end, it can be advantageous to have an excitation zone that extends a relatively short distance in the direction parallel to flow, and in some embodiments as short as about 1.7 microns or much shorter. Optical components can be constructed to create detection zones that extend across and beyond a channel in a direction perpendicular to flow and that extend a shorter distance in a direction parallel to flow. By way of example, an illuminator or the excitation signal can be shaped to produce an elliptical detection zone with a major axis extending across a channel and a minor axis extending along the channel. In one embodiment, the major axis is approximately 25 microns and the minor axis is approximately 1.7 microns. The effective focal length can be 2.5 mm, therefore the angular tolerance the beam 10 mrad or 0.5 degrees. In another embodiment, the detection zone is circular with a diameter of approximately 1.7 microns, (where approximately indicates +/−0.2 microns, when used with reference to the dimensions of a detection zone). However, it is to be appreciated that other shapes and sizes of detection zones are possible, as aspects of the present invention are not limited in this respect.

Figure 4:
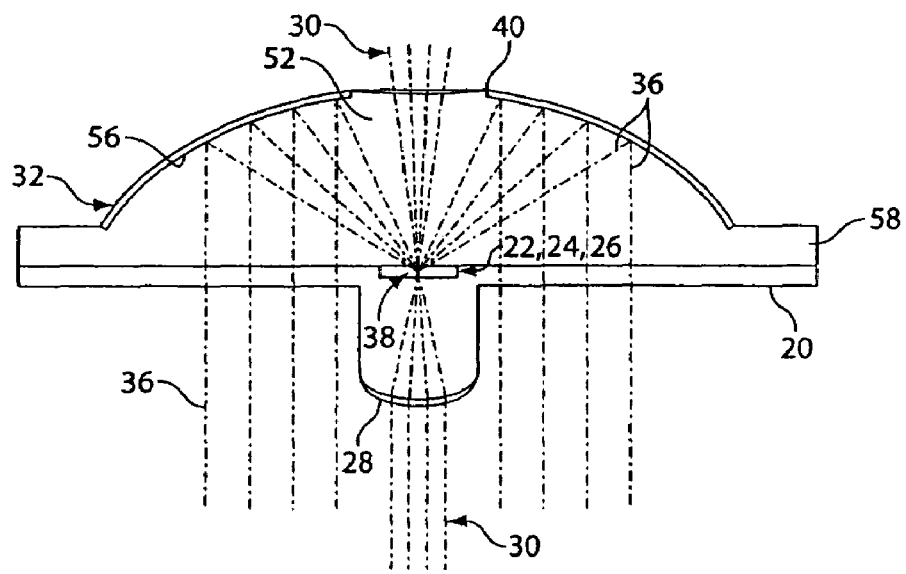
FIG. 4 is a cross sectional view of a chip with a refractive illuminator and a reflective collector located on opposed sides of the chip.

Optical components can be arranged in various ways about the chip to accomplish effects similar to those of the embodiment shown in FIG. 1. As shown in FIG. 4, the illuminator can be positioned on a different side of the channel than the collector. Here, the excitation signal is received by a refractive illuminator that focuses the excitation signal at the channel to create a detection zone. The concave, reflective collector has a focal point at the detection zone to receive a detection signal that will include emission signals from any agents present in the detection zone. As in the embodiment of FIG. 1, the concave reflector includes a central aperture through which the excitation signal passes to prevent the excitation signal from being reflected as a component of the detection signal. Due to the central aperture in the collector, the collector reflects an annulus of light toward the illuminator and ultimately toward a detector in the system. The excitation signal can pass through the center of the annulus to prevent the overlap of the excitation signal with the emission signals, as in the embodiment of FIG. 1.

Optical elements, such as a mirror or filters, can be used in embodiments of the invention to modify excitation, detection, and/or emission signals. By way of example, optical elements can include dichroic mirrors tuned to allow passage of light with wavelengths at that of the excitation signal, while reflecting light at wavelengths associated with expected emission signals. In one embodiment, the excitation signal passes through the dichroic mirror both when traveling from the illuminator to the detection zone and from the detection zone back toward the illuminator. However, spectral portions of the detection signal, that may include emission signals, are reflected by the dichroic mirror downstream toward a detector while portions of the detection signal at wavelengths associated with the excitation signal are not directed toward the detector.

In one embodiment, a mirror can include a central aperture positioned to allow passage of a portion of the detection signal that includes the excitation signal, while the surrounding mirror reflects spatial portions of the detection signal that do not include the excitation signal. In such an embodiment, excitation signals that have been overlapped with the emission signal are removed from the detection signal prior to reaching the detector.

Figure 5:
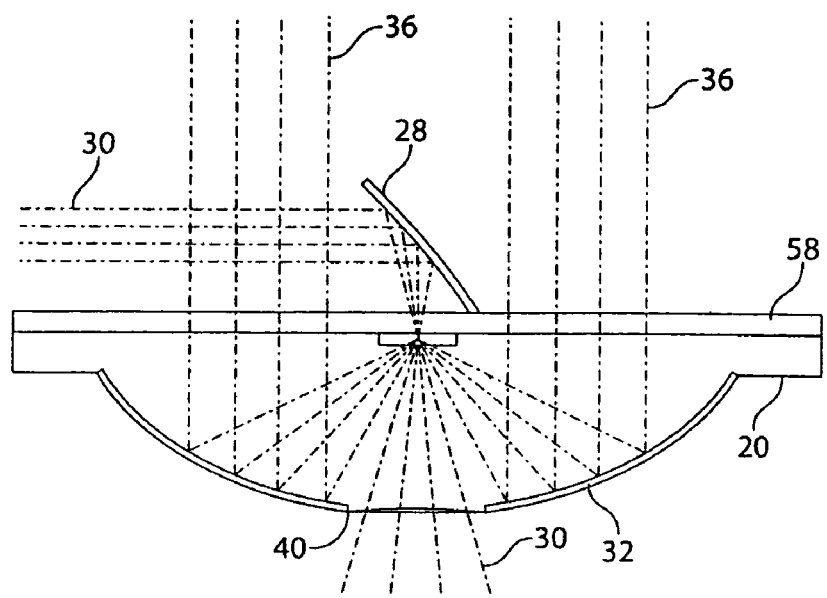
FIG. 5 is a cross sectional view of a chip with a reflective illuminator and a reflective collector located on opposed sides of the chip.

The chip can alternately incorporate a reflective illuminator and a collector on opposed sides of a channel, as shown in FIG. 5. The reflective illuminator directs an excitation signal received from the system towards the channel in the chip to define a detection zone. A concave, reflective collector receives a detection signal from the detection zone, including any emission signals from agents therein, and reflects the detection signal toward a downstream detector. In the embodiment illustrated in FIG. 5, the reflective collector includes an aperture positioned to allow passage of the excitation signal, such that the excitation signal is not reflected toward the downstream detector as a component of the detection signal. In alternate embodiments, the excitation signal can be removed from the detection signal by a filter, such as a dichroic mirror, or by a mirror that selectively reflects spatial portions of the detection signal that do not include the excitation signal, as described herein.

Figure 6:
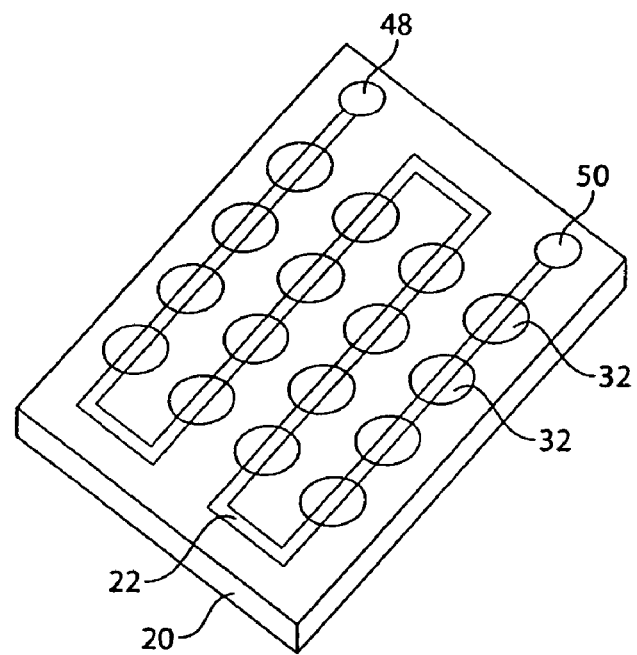
FIG. 6 is a perspective view of a chip with a plurality of pairs of collectors and illuminator pairs arranged in series along the length of a channel.
Figure 7:
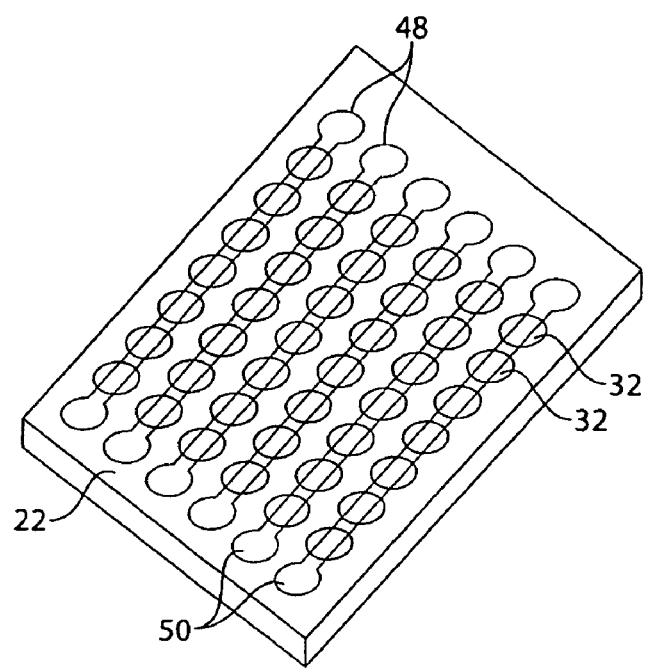
FIG. 7 is a perspective view of a chip with a plurality of pairs of collectors and illuminators arranged in parallel along a plurality of channels.

Chips can include a plurality of paired illuminators and collectors, along with other optical components, to increase the amount of information that can be obtained from a sample during an assay. In some embodiments, paired illuminators and collectors are positioned along the length of a common channel so that a sample passes through detection zones associated with each of the illuminators in a serial manner, like that illustrated in FIG. 6. In other embodiments, a chip includes multiple, separate channels each having one more pairs of collectors and illuminators. In some embodiments, such serially arranged detection zones can be used to produce redundant information about an agent, as described in U.S. Provisional Patent Application Ser. No. 60/630902 filed on Nov. 24, 2004, entitled LINEAR ANALYSIS OF POLYMERS, which is hereby incorporated by reference in its entirety. In some embodiments, serially arranged detection zones can be associated with different excitation signals, each tuned for the detection and/or analysis of a particular agent or label thereon. In this manner, multiple, different assays can be performed for different agents (or labels0 in a sample as the sample passes through the chip. Chips can also include multiple channels arranged in parallel to decrease sample throughput time in a chip, as shown in FIG. 7. Arranging channels in parallel allows more sample to be processed in an equivalent amount of time, all else constant. The channels can be fluidly connected to one another to allow a common sample to pass through each of the channels. In other embodiments, the chip includes multiple channels that are fluidly isolated from one another. Each of the isolated channels may have its own supply and exit port on the chip.

Samples may be passed through microfluidic devices in the system or the chip prior to being passed through a detection zone. Such microfluidic devices can be used to linearize or stretch an agent, like a polymer, prior to analysis. However, this may not be necessary if the ultimate detection system is capable of analyzing both stretched and condensed polymers. As used herein, stretching of the polymer means that the polymer is provided in a substantially linear extended form rather than a compacted, coiled and/or folded form. Stretching the polymer prior to analysis may be accomplished using any of the microfluidic devices or techniques discussed in U.S. patent application Ser. No. 10/821,664, filed on Apr. 9, 2004, entitled ADVANCED MICROFLUIDICS and published under publication no. US-2005-0112606-A1. These configurations may not be required if the target polymer can be analyzed in a compacted form.

Illuminators can also be incorporated into the chips of some embodiments. In some embodiments, a waveguide is embedded into the chip. The waveguide can pass adjacent to a channel in the chip to provide an evanescent excitation signal to the channel to define a detection zone. In some embodiments, a single waveguide can pass adjacent multiple channels, or multiple portions of a common channel to create multiple detection zones. In other embodiments, the waveguide terminates at the surface of the channel where it creates a detection zone. In such embodiments, the waveguide tapers as it approaches to create an evanescent excitation signal at the channel.

Figure 8:
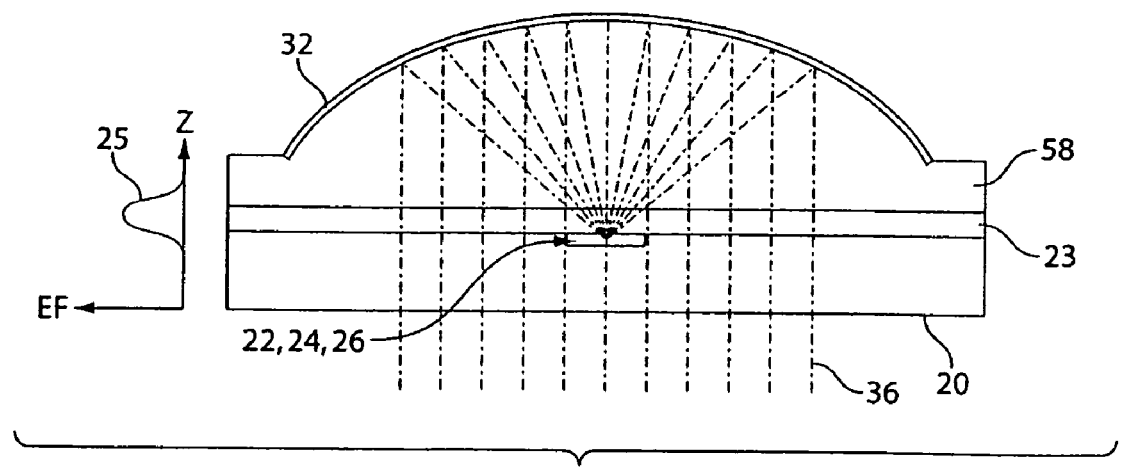
FIG. 8 is a cross sectional view of a waveguide incorporated into a chip.

FIG. 8 displays waveguide with evanescent field extending into the fluidic channel, according to one embodiment. The waveguide comprises a waveguide channel incorporated into the chip. The refractive index of the waveguide is higher than the refractive index of the chip. The evanescent field 25 of the waveguide extends through the depth of the fluidic channel. The evanescent field decays exponentially as a function of distance from the waveguide, typically within 200 nanometers for visible wavelengths. Therefore, in some embodiments, with channels that are deeper than 200 nanometers, only a portion the channel depth is illuminated. The waveguide channel may directly contact fluidic channel or the waveguide channel may be separated from the fluidic channel by a dielectric film. The waveguide channel may cross a plurality of fluidic channels. Embodiments that utilize a waveguide incorporated into the chip as an illuminator do not require a clear aperture to separate excitation signals from the detection signal, due to the evanescent nature of the excitation signal.

Samples can be derived from virtually any source known to contain or suspected of containing an agent of interest. Samples can be of solid, liquid or gaseous nature. They may be purified but usually are not. Different samples can be collected from different environments and prepared in the same manner by using the appropriate collecting device.

The samples to be tested can be a biological or bodily sample such as a tissue biopsy, urine, sputum, semen, stool, saliva and the like. The invention further contemplates preparation and analysis of samples that may be biowarfare targets. Air, liquids and solids that will come into contact with the greatest number of people are most likely to be biowarfare targets. Samples to be tested for the presence of such agents may be taken from an indoor or outdoor environment. Such biowarfare sampling can occur continuously, although this may not be necessary in every application. For example, in an airport setting, it may only be necessary to harvest randomly a sample near or around select baggage. In other instances, it may be necessary to continually monitor (and thus sample) the environment. These instances may occur in "heightened alert" states. In some important embodiments, the sample is tested for the presence of a pathogen. Samples can be tested for the presence of pathogenic substances such as but not limited to food pathogens, water-borne pathogens, and aerosolized pathogens.

Liquid samples can be taken from public water supplies, water reservoirs, lakes, rivers, wells, springs, and commercially available beverages. Solids such as food (including baby food and formula), money (including paper and coin currencies), public transportation tokens, books, and the like can also be sampled via swipe, wipe or swab testing and by placing the swipe, wipe or swab in a liquid for dissolution of any agents attached thereto. Based on the size of the swipe or swab and the volume of the corresponding liquid it must be placed in for agent dissolution, it may or may not be necessary to concentrate such liquid sample prior to further manipulation.

Air samples can be tested for the presence of normally airborne substances as well as aerosolized (or weaponized) chemicals or biologics that are not normally airborne. Air samples can be taken from a variety of places suspected of being biowarfare targets including public places such as airports, hotels, office buildings, government facilities, and public transportation vehicles such as buses, trains, airplanes, and the like.

The choice of air sampling instruments is dependent on user requirements, and those of ordinary skill in the art will be able to identify the appropriate instrument for a particular application. Various air sampling devices are currently commercially available, from companies such as BioAerosol Concentrator, International pbi S.pA., Meso Systems, Sceptor Industries, Inc., and Anderson. Moreover, techniques for air sampling are described in J. P. Lodge, Jr. Methods of Air Sampling and Analysis, Third Edition, Lewis Publishers, Inc. (Dec. 31, 1988) ISBN 0873711416.

The agent is any molecule to be detected using the systems and methods provided herein. It may be a biological or chemical in nature, but is not so limited. It may be naturally or non-naturally occurring, including agents synthesized ex vivo but released into a natural environment. Agents include but are not limited to proteins, nucleic acids, chemicals and the like. The agents may be biohazardous agents as described in greater detail herein. As described herein, the methods and systems of the invention can be used to detect one or more agents concurrently, simultaneously or consecutively. A plurality of agents is more than one and less than an infinite number. It includes less than $10^{10}$, less than $10^9$, less than $10^8$, less than $10^7$, less than $10^6$, less than $10^5$, less than $10^4$, less than 5000, less than 1000, les than 500, less 100, less than 50, less than 25, less than 10 and less than 5, as well as every integer therebetween as if explicitly recited herein.

The invention can be applied to the detection and optionally identification and/or quantification of any agent, but most preferably rare agents which would otherwise be costly to detect. One example of such agents is biohazardous or biowarfare agents. These agents can be biological or chemical in nature. Biological biowarfare agents can be classified broadly as pathogens (including spores thereof) or toxins. As used herein, a pathogen (including a spore thereof) is an agent capable of entering a subject such as a human and infecting that subject. Examples of pathogens include infectious agents such bacteria, viruses, fungi, parasites, mycobacteria and the like. Prions may also be considered pathogens to the extent they are thought to be the transmitting agent for CJD and like diseases. As used herein, a toxin is a pathogen-derived agent that causes disease and often death in a subject without also causing an infection. It derives from pathogens and so may be harvested therefrom. Alternatively, it may be synthesized apart from pathogen sources. Biologicals may be weaponized (i.e., aerosolized) for maximum spread.

In some embodiments, the agents are detected directly via the use of probes that bind to the agent itself. In other embodiments, the agents are detected via the use of probes that bind to agent specific components such as agent specific nucleic acids (e.g., DNA).

CDC Category A agents include *Bacillus anthracis* (otherwise known as anthrax), *Clostridium botulinum* and its toxin (causative agent for botulism), *Yersinia pestis* (causative agent for the plague), variola major (causative agent for small pox), *Francisella tularensis* (causative agent for tularemia), and viral hemorrhagic fever causing agents such as filoviruses *Ebola* and *Marburg* and arenaviruses such as *Lassa, Machupo* and *Junin*.

CDC Category B agents include Brucellosis (*Brucella* species), epsilon toxin of *Clostridium perfringens*, food safety threats such as *Salmonella* species, *E. coli* and *Shigella* Glanders (*Burkholderia mallei*), Melioidosis (*Burkholderia pseudomallei*), Psittacosis (*Chlamydia psittaci*), Q fever (*Coxiella burnetii*), ricin toxin (from *Ricinus communis*—castor beans), Staphylococcal enterotoxin B, Typhus fever (*Rickettsia prowazekii*), viral encephalitis (alphaviruses, e.g., Venezuelan equine encephalitis, eastern equine encephalitis, western equine encephalitis), and water safety threats such as e.g., *Vibrio cholerae, Cryptosporidium parvum*.

CDC Category C agents include emerging infectious diseases such as Nipah virus and hantavirus.

Further examples of bacteria that can be used as biohazards include Gonorrhea, *Staphylococcus* spp., *Streptococcus* spp. such as *Streptococcus pneumoniae*, Syphilis, *Pseudomonas* spp., *Clostridium difficile*, *Legionella* spp., *Pneumococcus* spp., *Haemophilus* spp. (e.g., *Haemophilus influenzae*), *Klebsiella* spp., *Enterobacter* spp., *Citrobacter* spp., *Neisseria* spp. (e.g., *N. meningitidis, N. gonorrhoeae*), *Shigella* spp., *Salmonella* spp., *Listeria* spp. (e.g., *L. monocytogenes*), *Pasteurella* spp. (e.g., *Pasteurella multocida*), *Streptobacillus* spp., *Spirillum* spp., *Treponema* spp. (e.g., *Treponema pallidum*), *Actinomyces* spp. (e.g., *Actinomyces israelli*), *Borrelia* spp., *Corynebacterium* spp., *Nocardia* spp., *Gardnerella* spp. (e.g., *Gardnerella vaginalis*), *Campylobacter* spp., *Spirochaeta* spp., *Proteus* spp., and *Bacteriodes* spp.

Further examples of viruses that can be used as biohazards include Hepatitis virus A, B and C, West Nile virus, poliovirus, rhinovirus, HIV, Herpes simplex virus 1 and 2 (including encephalitis, neonatal and genital forms), human papilloma virus, cytomegalovirus, Epstein Barr virus, Hepatitis virus A, B and C, rotavirus, adenovirus, influenza virus including influenza A virus, respiratory syncytial virus, varicella-zoster virus, small pox, monkey pox and SARS virus.

Further examples of fungi that can be used as biohazards include candidiasis, ringworm, histoplasmosis, blastomycosis, paracoccidioidomycosis, crytococcosis, aspergillosis, chromomycosis, mycetoma, pseudallescheriasis, and tinea versicolor.

Further examples of parasites that can be used as biohazards include both protozoa and nematodes such as amebiasis, *Trypanosoma cruzi*, Fascioliasis (e.g., *Facioloa hepatica*), Leishmaniasis, *Plasmodium* (e.g., *P. falciparum, P. knowlesi, P. malariae*), Onchocerciasis, Paragonimiasis, *Trypanosoma brucei, Pneumocystis* (e.g., *Pneumocystis carinii*), *Trichomonas vaginalis, Taenia, Hymenolepis* (e.g., *Hymenolepis nana*), *Echinococcus*, Schistosomiasis (e.g., *Schistosoma mansoni*), neurocysticercosis, *Necator americanus*, and *Trichuris trichuria, Giardia*.

Further examples of mycobacteria that can be used as biohazards include M. tuberculosis or M. leprae.

Examples of toxins include abrin, ricin and strychnine. Further examples of toxins include toxins produced by *Corynebacterium diphtheriae* (diphtheria), *Bordetella pertussis* (whooping cough), *Vibrio cholerae* (cholera), *Bacillus anthracis* (anthrax), *Clostridium botulinum* (botulism), *Clostridium tetani* (tetanus), and enterohemorrhagic *Escherichia coli* (bloody diarrhea and hemolytic uremic syndrome), *Staphylococcus aureus* alpha toxin, Shiga toxin (ST), cytotoxic necrotizing factor type 1 (CNF1), *E. coli* heat-stable toxin (ST), botulinum, tetanus neurotoxins, *S. aureus* toxic shock syndrome toxin (TSST), *Aeromonas hydrophila* aerolysin, *Clostridium perfringens* perfringolysin O, *E. coli* hemolysin, *Listeria monocytogenes* listeriolysin O, *Streptococcus pneumoniae* pneumolysin, *Streptococcus pyogenes* streptolysine O, *Pseudomonas aeruginosa* exotoxin A, *E. coli* DNF, *E. coli* LT, *E. coli* CLDT, *E. coli* EAST, *Bacillus anthracis* edema factor, *Bordetella pertussis* dermonecrotic toxin, *Clostridium botulinum* C2 toxin, *C. botulinum* C3 toxin, *Clostridium difficile* toxin A, and *C. difficile* toxin B.

Examples of chemicals that can be detected include arsenic, arsine, benzene, blister agents/vesicants, blood agents, bromine, borombenzylcyanide, chlorine, choking/lung/pulmonary agents, cyanide, distilled mustard, fentanyls and other opioids, mercury, mustard gas, nerve agents, nitrogen mustard, organic solvents, paraquat, phosgene, phosphine, sarin, sesqui mustard, stibine, sulfur mustard, warfarin, tabun, and the like.

The foregoing lists of infections are not intended to be exhaustive but rather exemplary.

It may be necessary to disrupt pathogen cell walls, cell membranes or viral envelopes, in some embodiments. This can enrich for agents to be detected. Disruption can be accomplished by any number of means including mechanical, electrical, osmotic, pressure, and the like. In one embodiment, the sample is exposed to an acoustic conditioning method.

As an example, microorganisms can be disrupted using a non-contact, reagent-less focused acoustic technology, developed at Covaris Inc., Woburn, Mass., and described in U.S. Pat. No. 6,719,449, issued Apr. 13, 2004. This procedure enables higher recoveries and better reproducibility than conventional, physical contact systems such as liquid nitrogen grinding, bead beating, sonicators (low frequency, unfocused, standing waves) and polytron-type homogenizers.

The agents may be processed using one or more reagents that acts on or reacts with and thereby modifies the agent. The nature of the reagents will vary depending on the processing step being performed with such reagent. The reagent may be a lysing agent (e.g., a detergent such as but not limited to deoxycholate), a labeling agent or probe (e.g., a sequence-specific nucleic acid probe), an enzyme (e.g., a nuclease such as a restriction endonuclease), an enzyme co-factor, a stabilizer (e.g., an anti-oxidant), and the like. One of ordinary skill in the art can envision other reagents to be used.

By way of example, a fluid may contain a lysing agent that lyses cellular agents (e.g., mammalian cells or pathogens such as bacteria, viruses and the like) in the channel, thereby releasing cellular contents, such as nucleic acids, into the channel. The fluids used in the invention may contain other components such as buffering compounds (e.g., TRIS), chelating compounds (e.g., EDTA), ions (e.g., monovalent, divalent or trivalent cations or anions), salts, and the like.

The agent may be a polymer. A "polymer" as used herein is a compound having a linear backbone to which monomers are linked together by linkages. The polymer is made up of a plurality of individual monomers. An individual monomer as used herein is the smallest building block that can be linked directly or indirectly to other building blocks (or monomers) to form a polymer. At a minimum, the polymer contains at least two linked monomers. The particular type of monomer will depend upon the type of polymer being analyzed. The polymer may be a nucleic acid, a peptide including a protein, a carbohydrate, an oligo- or polysaccharide, a lipid, etc.

In some embodiments, the polymer is capable of being bound to or by sequence- or structure-specific probes, wherein the sequence or structure recognized and bound by the probe is unique to that polymer or to a region of the polymer. It is possible to use a given probe for two or more polymers if a polymer is recognized by two or more probes, provided that the combination of probes is still specific for only a given polymer. The sample in some instances can be analyzed as is without harvest and isolation of polymers contained therein.

In some embodiments, the method can be used to detect a plurality of different polymers in a sample.

In some important embodiments, the agents are polymers such as nucleic acids. The term "nucleic acid" refers to multiple linked nucleotides (i.e., molecules comprising a sugar (e.g., ribose or deoxyribose) linked to an exchangeable organic base, which is either a pyrimidine (e.g., cytosine (C), thymidine (T) or uracil (U)) or a purine (e.g., adenine (A) or guanine (G)). "Nucleic acid" and "nucleic acid molecule" are used interchangeably and refer to oligoribonucleotides as well as oligodeoxyribonucleotides. The terms shall also include polynucleosides (i.e., a polynucleotide minus a phosphate) and any other organic base containing nucleic acid. The organic bases include adenine, uracil, guanine, thymine, cytosine and inosine.

In important embodiments, the nucleic acid is Deoxyribonucleic Acid (DNA) or Ribonucleic Acid (RNA). DNA includes genomic DNA (such as nuclear DNA and mitochondrial DNA), as well as in some instances complementary DNA (cDNA). RNA includes messenger RNA (mRNA), miRNA, siRNA and the like. Non-naturally occurring nucleic acids include but are not limited to bacterial artificial chromosomes (BACs) and yeast artificial chromosomes (YACs). Harvest and isolation of nucleic acids are routinely performed in the art and suitable methods can be found in standard molecular biology textbooks. (See, for example, Maniatis' Handbook of Molecular Biology.)

Preferably, prior amplification using techniques such as polymerase chain reaction (PCR) are not necessary. Accordingly, the polymer may be a non in vitro amplified nucleic acid. As used herein, a "non in vitro amplified nucleic acid" refers to a nucleic acid that has not been amplified in vitro using techniques such as polymerase chain reaction or recombinant DNA methods. A non in vitro amplified nucleic acid may however be a nucleic acid that is amplified in vivo (in the biological sample from which it was harvested) as a natural consequence of the development of the cells in vivo. This means that the non in vitro nucleic acid may be one which is amplified in vivo as part of locus amplification, which is commonly observed in some cell types as a result of mutation or cancer development.

As used herein with respect to linked units of a polymer including a nucleic acid, "linked" or "linkage" means two entities bound to one another by any physicochemical means. Any linkage known to those of ordinary skill in the art, covalent or non-covalent, is embraced. Natural linkages, which are those ordinarily found in nature connecting for example the individual units of a particular nucleic acid, are most common. Natural linkages include, for instance, amide, ester and thioester linkages. The individual units of a nucleic acid analyzed by the methods of the invention may be linked, however, by synthetic or modified linkages. Nucleic acids where the units are linked by covalent bonds will be most common but those that include hydrogen bonded units are also embraced by the invention. It is to be understood that all possibilities regarding nucleic acids apply equally to nucleic acid targets and nucleic acid probes, as discussed herein.

The nucleic acids may be double-stranded, although in some embodiments the nucleic acid targets are denatured and presented in a single-stranded form. This can be accomplished by modulating the environment of a double-stranded nucleic acid including singly or in combination increasing temperature, decreasing salt concentration, and the like. Methods of denaturing nucleic acids are known in the art.

The target nucleic acids commonly have a phosphodiester backbone because this backbone is most common in vivo. However, they are not so limited. Backbone modifications are known in the art. One of ordinary skill in the art is capable of preparing such nucleic acids without undue experimentation. The probes, if nucleic acid in nature, can also have backbone modifications such as those described herein.

Thus the nucleic acids may be heterogeneous in backbone composition thereby containing any possible combination of nucleic acid units linked together such as peptide nucleic acids (which have amino acid linkages with nucleic acid bases, and which are discussed in greater detail herein). In some embodiments, the nucleic acids are homogeneous in backbone composition.

The methods of the invention in part may be used to analyze agents using probes that recognize and specifically bind to an agent. Binding of a probe to an agent may indicate the presence and location of a target site in the target agent, or it may simply indicate the presence of the agent, depending on user requirements. As used herein, a target agent that is bound by a probe is "labeled" with the probe and/or its detectable label.

As used herein, a probe is a molecule or compound that binds preferentially to the agent of interest (i.e., it has a greater affinity for the agent of interest than for other compounds). Its affinity for the agent of interest may be at least 2-fold, at least 5-fold, at least 10-fold, or more than its affinity for another compound. Probes with the greatest differential affinity are preferred in most embodiments.

The probes can be of any nature including but not limited to nucleic acid (e.g., aptamers), peptide, carbohydrate, lipid, and the like. A nucleic acid based probe such as an oligonucleotide can be used to recognize and bind DNA or RNA. The nucleic acid based probe can be DNA, RNA, Locked Nucleic Acid (LNA) or Peptide Nucleic Acid (PNA), although it is not so limited. It can also be a combination of one or more of these elements and/or can comprise other nucleic acid mimics. With the advent of aptamer technology, it is possible to use nucleic acid based probes in order to recognize and bind a variety of compounds, including peptides and carbohydrates, in a structurally, and thus sequence, specific manner. Other probes for nucleic acid targets include but are not limited to sequence-specific major and minor groove binders and intercalators, nucleic acid binding peptides or proteins, etc.

As used herein a "peptide" is a polymer of amino acids connected preferably but not solely with peptide bonds. The probe may be an antibody or an antibody fragment. Antibodies include IgG, IgA, IgM, IgE, IgD as well as antibody variants such as single chain antibodies. Antibody fragments contain an antigen-binding site and thus include but are not limited to Fab and F(ab)$_2$ fragments.

The methods provided herein involve the use of probes that bind to the target polymer in a sequence-specific manner. "Sequence-specific" when used in the context of a nucleic acid means that the probe recognizes a particular linear (or in some instances quasi-linear) arrangement of nucleotides or derivatives thereof. In some embodiments, the probes are "polymer-specific" meaning that they bind specifically to a particular polymer, possibly by virtue of a particular sequence or structure unique to that polymer.

In some instances, nucleic acid probes will form at least a Watson-Crick bond with a target nucleic acid. In other instances, the nucleic acid probe can form a Hoogsteen bond with the target nucleic acid, thereby forming a triplex. Examples of these latter probes include molecules that recognize and bind to the minor and major grooves of nucleic acids (e.g., some forms of antibiotics). In some embodiments, the nucleic acid probes can form both Watson-Crick and Hoogsteen bonds with the nucleic acid polymer. BisPNA probes, for instance, are capable of both Watson-Crick and Hoogsteen binding to a nucleic acid.

The nucleic acid probes of the invention can be any length ranging from at least 4 nucleotides to in excess of 1000 nucleotides. The length of the probe can be any length of nucleotides between and including the ranges listed herein, as if each and every length was explicitly recited herein.

The probes are preferably single-stranded, but they are not so limited.

The nucleic acid probe hybridizes to a complementary sequence within the nucleic acid polymer. The specificity of binding can be manipulated based on the hybridization conditions. For example, salt concentration and temperature can be modulated in order to vary the range of sequences recognized by the nucleic acid probes. Those of ordinary skill in the art will be able to determine optimum conditions for a desired specificity.

In some embodiments, the probes may be molecular beacons. When not bound to their targets, the molecular beacon probes form a hairpin structure and do not emit fluorescence since one end of the molecular beacon is a quencher molecule. However, when bound to their targets, the fluorescent and quenching ends of the probe are sufficiently separated so that the fluorescent end can now emit.

The probes may be nucleic acids, as described herein, or nucleic acid derivatives. As used herein, a "nucleic acid derivative" is a non-naturally occurring nucleic acid or a unit thereof. Nucleic acid derivatives may contain non-naturally occurring elements such as non-naturally occurring nucleotides and non-naturally occurring backbone linkages. These include substituted purines and pyrimidines such as C-5 propyne modified bases, 5-methylcytosine, 2-aminopurine, 2-amino-6-chloropurine, 2,6-diaminopurine, hypoxanthine, 2-thiouracil and pseudoisocytosine. Other such modifications are well known to those of skill in the art.

The nucleic acid derivatives may also encompass substitutions or modifications, such as in the bases and/or sugars. For example, they include nucleic acids having backbone sugars which are covalently attached to low molecular weight organic groups other than a hydroxyl group at the 3' position and other than a phosphate group at the 5' position. Thus, modified nucleic acids may include a 2'-O-alkylated ribose group. In addition, modified nucleic acids may include sugars such as arabinose instead of ribose.

In some embodiments, the probe is a nucleic acid that is a PNA, a bisPNA clamp, a pseudocomplementary PNA, a locked nucleic acid (LNA), DNA, RNA, or co-nucleic acids of the above such as DNA-LNA co-nucleic acids. siRNA or miRNA or RNAi molecules can be similarly used.

In some embodiments, the probe is a peptide nucleic acid (PNA), a bisPNA clamp, a locked nucleic acid (LNA), a ssPNA, a pseudocomplementary PNA (pcPNA), a two-armed PNA (as described in co-pending U.S. Patent Application having Ser. No. 10/421,644 and publication number US 2003-0215864 A1 and published Nov. 20, 2003, and PCT application having serial number PCT/US03/12480 and publication number WO 03/091455 A1 and published Nov. 6, 2003, filed on Apr. 23, 2003), or co-polymers thereof (e.g., a DNA-LNA co-polymer).

As stated herein, the agent may be labeled either by binding a probe. As an example, if the agent is a nucleic acid, it may be labeled through the use of sequence-specific probes that bind to the polymer in a sequence-specific manner. The sequence-specific probes are labeled with a detectable label. The nucleic acid however can also be synthesized in a manner that incorporates detectable labels directly into the growing nucleic acid. For example, this latter labeling can be accomplished by chemical means or by the introduction of active amino or thiol groups into nucleic acids. (Proudnikov and Mirabekov, Nucleic Acid Research, 24:4535-4532, 1996.) An extensive description of modification procedures that can be performed on a nucleic acid polymer can be found in Hermanson, G. T., Bioconjugate Techniques, Academic Press, Inc., San Diego, 1996, which is incorporated by reference herein.

There are several known methods of direct chemical labeling of DNA (Hermanson, 1996; Roget et al., 1989; Proudnikov and Mirabekov, 1996). One of the methods is based on the introduction of aldehyde groups by partial depurination of DNA. Fluorescent labels with an attached hydrazine group are efficiently coupled with the aldehyde groups and the hydrazine bonds are stabilized by reduction with sodium labeling efficiencies around 60%. The reaction of cytosine with bisulfite in the presence of an excess of an amine fluorophore leads to transamination at the N4 position (Hermanson, 1996). Reaction conditions such as pH, amine fluorophore concentration, and incubation time and temperature affect the yield of products formed. At high concentrations of the amine fluorophore (3M), transamination can approach 100% (Draper and Gold, 1980).

In addition to the above method, it is also possible to synthesize nucleic acids de novo (e.g., using automated nucleic acid synthesizers) using fluorescently labeled nucleotides. Such nucleotides are commercially available from suppliers such as Amersham Pharmacia Biotech, Molecular Probes, and New England Nuclear/Perkin Elmer.

Probes are generally labeled with a detectable label. A detectable label is a moiety, the presence of which can be ascertained directly or indirectly. Generally, detection of the label involves the creation of a detectable signal such as for example an emission of energy. The label may be of a chemical, peptide or nucleic acid nature although it is not so limited. The nature of label used will depend on a variety of factors, including the nature of the analysis being conducted, the type of the energy source and detector used and the type of polymer and probe. The label should be sterically and chemically compatible with the constituents to which it is bound.

The label can be detected directly for example by its ability to emit and/or absorb electromagnetic radiation of a particular wavelength. A label can be detected indirectly for example by its ability to bind, recruit and, in some cases, cleave another moiety which itself may emit or absorb light of a particular wavelength (e.g., an epitope tag such as the FLAG epitope, an enzyme tag such as horseradish peroxidase, etc.). Generally the detectable label can be selected from the group consisting of directly detectable labels such as a fluorescent molecule (e.g., fluorescein, rhodamine, tetramethylrhodamine, R-phycoerythrin, Cy-3, Cy-5, Cy-7, Texas Red, Phar-Red, allophycocyanin (APC), fluorescein amine, eosin, dansyl, umbelliferone, 5-carboxyfluorescein (FAM), 2'7'-dimethoxy-4'5'-dichloro-6-carboxyfluorescein (JOE), 6 carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), 5-(2'-aminoethyl) aminonaphthalene-1-sulfonic acid (EDANS), 4-acetamido-4'-isothiocyanatostilbene-2,2'disulfonic acid, acridine, acridine isothiocyanate, r-amino-N-(3-vinylsulfonyl)phenylnaphthalimide-3,5, disulfonate (Lucifer Yellow VS), N-(4-anilino-1-naphthyl)maleimide, anthranilamide, Brilliant Yellow, coumarin, 7-amino-4-methylcoumarin, 7-amino-4-trifluoromethylcouluarin (Coumarin 151), cyanosine, 4',6-diaminidino-2-phenylindole (DAPI), 5',5"-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin diethylenetriamine pentaacetate, 4,4'-diisothiocyanatodihydro-stilbene-2,2'-disulfonic acid, 4,4'-diisothiocyanatostilbene-2,2'-disulfonic acid, 4-dimethylaminophenylazophenyl-4'-isothiocyanate (DABITC), eosin isothiocyanate, erythrosin B, erythrosin isothiocyanate, ethidium, 5-(4,6-dichlorotriazin-2-yl) aminofluorescein (DTAF), QFITC (XRITC), fluorescamine, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4 (Cibacron .RTM. Brilliant Red 3B-A), lissamine rhodamine B sulfonyl chloride, rhodamine B, rhodamine 123, rhodamine X, sulforhodamine B, sulforhodamine 101, sulfonyl chloride derivative of sulforhodamine 101, tetramethyl rhodamine, riboflavin, rosolic acid, and terbium chelate derivatives), a chemiluminescent molecule, a bioluminescent molecule, a chromogenic molecule, a radioisotope (e.g., $P^{32}$ or $H^3$, $^{14}C$, $^{125}I$ and $^{131}I$), an electron spin resonance molecule (such as for example nitroxyl radicals), an optical or electron density molecule, an electrical charge transducing or transferring molecule, an electromagnetic molecule such as a magnetic or paramagnetic bead or particle, a semiconductor nanocrystal or nanoparticle (such as quantum dots described for example in U.S. Pat. No. 6,207,392 and commercially available from Quantum Dot Corporation and Evident Technologies), a colloidal metal, a colloid gold nanocrystal, a nuclear magnetic resonance molecule, and the like.

The detectable label can also be selected from the group consisting of indirectly detectable labels such as an enzyme (e.g., alkaline phosphatase, horseradish peroxidase, β-galactosidase, glucoamylase, lysozyme, luciferases such as firefly luciferase and bacterial luciferase (U.S. Pat. No. 4,737,456); saccharide oxidases such as glucose oxidase, galactose oxidase, and glucose-6-phosphate dehydrogenase; heterocyclic oxidases such as uricase and xanthine oxidase coupled to an enzyme that uses hydrogen peroxide to oxidize a dye precursor such as HRP, lactoperoxidase, or microperoxidase), an enzyme substrate, an affinity molecule, a ligand, a receptor, a biotin molecule, an avidin molecule, a streptavidin molecule, an antigen (e.g., epitope tags such as the FLAG or HA epitope), a hapten (e.g., biotin, pyridoxal, digoxigenin fluorescein and dinitrophenol), an antibody, an antibody fragment, a microbead, and the like. Antibody fragments include Fab, $F(ab)_2$, Fd and antibody fragments which include a CDR3 region.

In some embodiments, the detectable label is a member of a FRET fluorophore pair. FRET fluorophore pairs are two fluorophores that are capable of undergoing FRET to produce or eliminate a detectable signal when positioned in proximity to one another. Examples of donors include Alexa 488, Alexa 546, BODIPY 493, Oyster 556, Fluor (FAM), Cy3 and TMR (Tamra). Examples of acceptors include Cy5, Alexa 594, Alexa 647 and Oyster 656. Cy5 can work as a donor with Cy3, TMR or Alexa 546, as an example. FRET should be possible with any fluorophore pair having fluorescence maxima spaced at 50-100 nm from each other.

The polymer may be labeled in a sequence non-specific manner. For example, if the polymer is a nucleic acid such as DNA, then its backbone may be stained with a backbone label. Examples of backbone stains that label nucleic acids in a sequence non-specific manner include intercalating dyes such as phenanthridines and acridines (e.g., ethidium bromide, propidium iodide, hexidium iodide, dihydroethidium, ethidium homodimer-1 and -2, ethidium monoazide, and ACMA); minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc.

Still other examples of nucleic acid stains include the following dyes from Molecular Probes: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), STYO-81,-80, -82, -83, -84, -85 (orange), SYTO-64, -17, -59, -61, -62, -60, -63 (red).

The detection system may be configured as a single molecule analysis system (e.g., a single polymer analysis system). A single molecule detection system is capable of analyzing single molecules separately from other molecules. Such a system may be capable of analyzing single molecules in a linear manner and/or in their totality. In certain embodiments in which detection is based predominately on the presence or absence of a signal, linear analysis may not be required. However, there are other embodiments embraced by the invention which would benefit from the ability to analyze linearly molecules (preferably nucleic acids) in a sample. These include applications in which the sequence of the nucleic acid is desired, or in which the polymers are distinguished based on spatial labeling pattern rather than a unique detectable label.

Thus, the polymers can be analyzed using linear polymer analysis systems. A linear polymer analysis system is a system that analyzes polymers such as nucleic acids, in a linear manner (i.e., starting at one location on the polymer and then proceeding linearly in either direction therefrom). As a polymer is analyzed, the detectable labels attached to it are detected in either a sequential or simultaneous manner. When detected simultaneously, the signals usually form an image of the polymer, from which distances between labels can be determined. When detected sequentially, the signals are viewed in histogram (signal intensity vs. time) that can then be translated into a map, with knowledge of the velocity of the polymer. It is to be understood that in some embodiments, the polymer is attached to a solid support, while in others it is free flowing. In either case, the velocity of the polymer as it moves past, for example, an interaction station or a detector, will aid in determining the position of the labels relative to each other and relative to other detectable markers that may be present on the polymer.

An example of a suitable system is the GeneEngine™ (U.S. Genomics, Inc., Woburn, Mass.). The Gene Engine™ system is described in PCT patent applications WO98/35012 and WO00/09757, published on Aug. 13, 1998, and Feb. 24, 2000, respectively, and in issued U.S. Pat. No. 6,355,420 B1, issued Mar. 12, 2002. The contents of these applications and patent, as well as those of other applications and patents, and references cited herein are incorporated by reference herein in their entirety. This system is both a single molecule analysis system and a linear polymer analysis system. It allows, for example, single nucleic acids to be passed through an interaction station in a linear manner, whereby the nucleotides in the nucleic acid are interrogated individually in order to determine whether there is a detectable label conjugated to the nucleic acid. Interrogation involves exposing the nucleic acid to an energy source such as optical radiation of a set wavelength. The mechanism for signal emission and detection will depend on the type of label sought to be detected, as described herein.

The nature of such detection systems will depend upon the nature of the detectable moiety used to label the polymer. The detection system can be selected from any number of detection systems known in the art. These include an electron spin resonance (ESR) detection system, a charge coupled device (CCD) detection system, a fluorescent detection system, an electrical detection system, a photographic film detection system, a chemiluminescent detection system, an enzyme detection system, an atomic force microscopy (AFM) detection system, a scanning tunneling microscopy (STM) detection system, an optical detection system, a nuclear magnetic resonance (NMR) detection system, a near field detection system, and a total internal reflection (TIR) detection system, many of which are electromagnetic detection systems.

Optical detectable signals are generated, detected and stored in a database. The signals can be analyzed to determine structural information about the polymer. The signals can be analyzed by assessing the intensity of the signal to determine structural information about the polymer. The computer may be the same computer used to collect data about the polymers, or may be a separate computer dedicated to data analysis. A suitable computer system to implement embodiments of the present invention typically includes an output device which displays information to a user, a main unit connected to the output device and an input device which receives input from a user. The main unit generally includes a processor connected to a memory system via an interconnection mechanism. The input device and output device also are connected to the processor and memory system via the interconnection mechanism. Computer programs for data analysis of the detected signals are readily available from CCD (Charge Coupled Device) manufacturers.

Other interactions involved in methods of the invention will produce a nuclear radiation signal. As a radiolabel on a polymer passes through the defined region of detection, nuclear radiation is emitted, some of which will pass through the defined region of radiation detection. A detector of nuclear radiation is placed in proximity of the defined region of radiation detection to capture emitted radiation signals. Many methods of measuring nuclear radiation are known in the art including cloud and bubble chamber devices, constant current ion chambers, pulse counters, gas counters (i.e., Geiger-Müller counters), solid state detectors (surface barrier detectors, lithium-drifted detectors, intrinsic germanium detectors), scintillation counters, Cerenkov detectors, to name a few.

Other types of signals generated are well known in the art and have many detections means which are known to those of skill in the art. Some of these include opposing electrodes, magnetic resonance, and piezoelectric scanning tips. Opposing nanoelectrodes can function by measurement of capacitance changes. Two opposing electrodes create an area of energy storage, located effectively between the two electrodes. It is known that the capacitance of such a device changes when different materials are placed between the electrodes. This dielectric constant is a value associated with the amount of energy a particular material can store (i.e., its capacitance). Changes in the dielectric constant can be measured as a change in the voltage across the two electrodes. In the present example, different nucleotide bases or unit specific markers of a polymer may give rise to different dielectric constants. The capacitance changes as the dielectric constant of the unit specific marker of the polymer per the equation: $C=KC_o$, where K is the dielectric constant and $C_o$ is the capacitance in the absence of any bases. The voltage deflection of the nanoelectrodes is then outputted to a measuring device, recording changes in the signal with time.

Equivalents

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the invention. The advantages and objects of the invention are not necessarily encompassed by each embodiment of the invention.

What is claimed is:

1. A chip for use in detecting an agent, the chip comprising:
   a microfluidic channel incorporated into the chip, the microfluidic channel adapted to deliver a fluid that may contain an agent to a detection zone that lies at least partially in the channel;
   an illuminator incorporated into the chip, the illuminator adapted to direct an excitation signal to the detection zone; and
   a concave reflector incorporated into the chip and having a focal point at the detection zone, the concave reflector constructed and arranged to receive an emission signal from the agent when present in the detection zone and to reflect the emission signal to a detector.

2. The chip of claim 1, wherein the concave reflector is incorporated into the chip in a fixed relationship with respect to the channel.

3. The chip of claim 2, further comprising:
   a solid medium that provides a pathway from the microfluidic channel to the concave reflector along which the emission signal can travel without substantial refraction.

4. The chip of claim 3, wherein the solid medium extends from a wall of the channel to the concave reflector.

5. The chip of claim 3, further comprising:
   a cover slip adapted to mate with the chip to enclose the channel, the concave reflector being incorporated into the cover slip.

6. The chip of claim 1, wherein the illuminator and the concave reflector are on opposed sides of the channel.

7. The chip of claim 1, wherein the illuminator includes a refractive illuminator having a focal point substantially located at the focal point of the concave reflector and further wherein the illuminator and the concave reflector are positioned on a common side of the channel.

8. The chip of claim 7, wherein the illuminator and the concave reflector are constructed and arranged such that overlap of the excitation signal and the emission signal is minimized.

9. The chip of claim 8 wherein the concave reflector includes a central aperture and further wherein the refractive illuminator is positioned at the central aperture.

10. The chip of claim 1, wherein the concave reflector has a collection half angle greater than 49 degrees within water in a rectangular channel.

11. The chip of claim 1, wherein the reflector has a collector numerical aperture of 1.0 or greater.

12. The chip of claim 1, comprising a plurality of pairs of concave reflectors and illuminators, each pair associated with a corresponding detection zone.

13. The chip of claim 1, wherein the illuminator has an illuminator numerical aperture between 0.18 and 0.20.

14. The chip of claim 1, further comprising:
   a registration feature for aligning the reflector relative to the detection zone.

15. A chip for use in detecting an agent, the chip comprising:
   a microfluidic channel incorporated into the chip, the microfluidic channel adapted to deliver a fluid that may contain an agent to a plurality of detection zones that each lie at least partially in the channel;
   a plurality of concave reflectors incorporated into the chip and each held in a fixed relationship with respect to one of the plurality of detection zones; and
   a plurality of illuminators incorporated into the chip, each of the plurality of illuminators adapted to provide an excitation signal to one of the plurality of detection zones.

16. A method for detecting an agent, the method comprising:
   providing a chip comprising:
      a microfluidic channel incorporated into the chip, the microfluidic channel adapted to deliver a fluid containing an agent to a detection zone that lies at least partially in the channel;
      an illuminator incorporated into the chip, the illuminator adapted to direct an excitation signal to the detection zone; and
      a concave reflector incorporated into the chip and having a focal point at the detection zone; the concave reflector constructed and arranged to receive emission signals from the agent when present in the detection zone and to reflect the emissions signals toward a detector;
   providing a fluid that may contain the agent to the channel;
   illuminating the detection zone with the excitation signal to cause any agent present in the detection zone to emit an emission signal;
   receiving the emission signal with the concave reflector; and
   reflecting the emission signal toward the detector to determine whether the agent is present in the detection zone.

17. The method of claim 16, wherein the chip includes a plurality of concave reflectors and illuminators each associated with one of a plurality of detection zones at the channel, further wherein providing the fluid that may contain the agent comprises providing the fluid to each of the plurality of detection zones.

18. A method for detecting an agent, the method comprising:
   providing a chip comprising:
      a microfluidic channel incorporated into the chip, the microfluidic channel adapted to deliver a fluid that may contain an agent to a detection zone that lies at least partially in the channel; and
      a concave reflector incorporated into the chip in fixed relationship with respect to the channel and having a focal point at the detection zone, the concave reflector constructed and arranged to receive an emission signal from the agent when present in the detection zone and to reflect the emission signal toward a detector;
   providing a fluid that may contain the agent to the channel;

illuminating the detection zone with the excitation signal to cause any agent present in the detection zone to emit an emission signal;

receiving the emission signal with the concave reflector; and reflecting the emission signal toward the detector to determine whether the agent is present in the detection zone.

19. The method of claim 18, wherein the chip includes a plurality of concave reflectors and illuminators each associated with one of a plurality of detection zones at the channel, further wherein providing the fluid that may contain the agent comprises providing the fluid to each of the plurality of detection zones.

20. A method for detecting an agent, the method comprising directing an excitation signal toward an illuminator incorporated into a chip;

focusing the excitation signal to a detection zone at a channel incorporated into the chip;

exciting an agent present in the detection zone such that the agent emits an emission signal;

receiving the emission signal with a collector that is incorporated into the chip; and reflecting the emission signal toward a downstream detector that is separate from the chip.

* * * * *